United States Patent [19]

Kostich

[11] Patent Number: 5,707,572

[45] Date of Patent: Jan. 13, 1998

[54] METHOD FOR IMMOBILIZING THE CENTRAL NERVOUS SYSTEM OF THE HUMAN ANATOMY

[76] Inventor: Jeffrey Vincent Kostich, 7992 Pine Ridge St. NW., North Canton, Ohio 44720

[21] Appl. No.: 597,366

[22] Filed: Feb. 8, 1996

[51] Int. Cl.$^6$ .................................................. B29C 44/02
[52] U.S. Cl. .................. 264/46.4; 264/45.2; 264/46.5; 264/46.6; 264/222; 264/DIG. 30
[58] Field of Search ........................ 264/45.2, 46.4, 264/46.5, 46.6, 222, DIG. 30; 425/2

[56] References Cited

U.S. PATENT DOCUMENTS

| | | |
|---|---|---|
| 3,048,169 | 8/1962 | Pierce . |
| 3,403,676 | 10/1968 | Gibbons . |
| 4,347,213 | 8/1982 | Rogers, Jr. . |
| 4,450,122 | 5/1984 | Gallina . |
| 4,622,185 | 11/1986 | Kostich . |
| 4,905,267 | 2/1990 | Miller et al. ............... 378/208 |
| 5,454,993 | 10/1995 | Kostich . |

OTHER PUBLICATIONS

"Stabilization Device For Patient's Undergoing Radiation Therapy for Hodgkin's Disease." by Gunilla C. Bentel; Duke University Medical Center; Durham, North Carolina (undated).

"Stabilization Device For Patient's Undergoing Radiation Therapy For Carcinoma Of The Breast." by Gunilla C. Bentel; Duke University Medical Center; Durham, North Carolina (undated).

IBM Technical Disclosure Bulletin, vol. 12 No. 4 Sep. 4, 1969: "Blown Polyurethane Medical Casts" by B.P. Hall and D.A. Moore.

*Primary Examiner*—Allan R. Kuhns
*Attorney, Agent, or Firm*—Oldham & Oldham Co., LPA

[57] ABSTRACT

An apparatus for immobilizing and positioning the head, shoulder, and torso region of the human anatomy when in the prone position for radiographic examination or treatment. The device consists of a base board, a face support, a pair head side walls, a pair of shoulder walls, and a pair of body side walls. A foam mixture is applied to the upper surface of the base and the entire device is placed into a large flexible container or bag. A patient's head, shoulder and torso region are placed on the device in a prone position. The patient remains in a fixed position while the foam mixture expands around the patient's body and the apparatus. After a brief period of time, the foam sets or hardens and a mold or template is formed. This mold serves to immobilize the head, shoulder and torso region of the body when in a prone position during radiographic examinations and treatment as well as other procedures. The form can be utilized repeatedly with the same patient in subsequent procedure for duplicating the initial examination or treatment posture.

12 Claims, 2 Drawing Sheets

METHOD FOR IMMOBILIZING THE CENTRAL NERVOUS SYSTEM OF THE HUMAN ANATOMY

TECHNICAL FIELD

This invention relates generally to an apparatus and method for immobilizing a portion of the human anatomy for procedures such as radiographic examinations and treatment. More specifically, the present invention relates to a method and apparatus for developing a mold or template of the head, shoulder and torso of the human anatomy in the prone position for treatment of the central nervous system.

BACKGROUND OF THE INVENTION

The efficiency and effectiveness of certain medical procedures can be considerably enhanced if that portion, or those portions, of the patient's anatomy requiring treatment can be quickly and accurately positioned and comfortably supported during successive treatments. This need to be able to accurately position, and successively reposition, a portion of the patent's anatomy and then maintain it virtually motionless is exemplified by considering a series of radiation treatments. The radiation beam must be projected to an exact location, sometimes interiorly of the body. Such a radiation beam must be most accurate in order not to inflict damage to the tissues surrounding the area to be treated, and as a result there is little margin for error. Not only must the radiation beam be projected accurately toward a particular spot on the body surface, the body must also be precisely oriented to effect the required alignment of the radiation beam from the surface of the body to the interiorly located tissue being treated. Moreover, once the patient is positioned and aligned he/she, must remain as motionless as possible. Radiation treatment generally requires repeated exposures over a period of several weeks. Thus, the difficulties are compounded without a template by which medical personnel can quickly and accurately reposition and support the patient during successive treatments in exactly the same position as initially determined.

Previously, standardized forms have been used which approximate the size of selected portions of the human anatomy. A foam is poured into the form, the patient is positioned within the form, and the foam rises around the contours of the patient and is restricted by the walls of the form. This approach is deficient in that these forms are available in a limited number of standard sizes, typically only pediatric and adult, and, therefore, are not always suitable for a particular patient. Further, the mere size of the standardized forms makes it impractical for a healthcare facility to stock an adequate quantity of numerous sized forms.

Based on these deficiencies, the applicant developed the invention disclosed in U.S. Pat. No. 4,622,185 as a "Method and Apparatus for Molding and Accurately Repositioning Selected Portions of the Human Anatomy", the substance of which is herein incorporated by reference. The device disclosed in that patent consisted essentially of a base containing a plurality of orthogonally disposed grooves or slots. A plurality of slats are provided for removable insertion into the grooves. The slats are cooperatively aligned to substantially encompass the area immediately around that particular portion of the patient's anatomy for which a template is to be formed. A flexible container or bag is placed within the area defined by the slats and a predetermined amount of foam is placed therein. The portion of the patient's body to be molded is placed over the foam filled container and the foam expands around the selected portion of the patient's body. This apparatus and technique is highly versatile and has enjoyed widespread acceptance in the medical community but is not practical when used to create forms with a patient in the prone position as is needed when treating patients with maladies affecting the central nervous system such as medulloblastoma, lymphoma or leukemia.

To treat such maladies, patients require therapy such as cranio-spinal irradiation (CSI). Patients requiring CSI are usually children or young adults since these tumors most frequently occur in the relatively young population. The technique applied in the treatment of CSI usually requires that the patient is in the prone position while the brain and cervical spine is treated through opposed lateral fields and the spinal axis through one or two posterior fields.

For most patients, the prone position is less comfortable than the supine and is therefore less likely to be maintained throughout a treatment session unless the patient is positioned in some type of body shell. Children often move unintentionally and if they are in an uncomfortable position the risk of movement is increased. In addition, patients can become uncomfortable when their eyes are covered and or when their breathing path is partially blocked. As a result a patient is more likely to try to move their head in search of a clear air passageway which can impact on the effectiveness of the treatment.

Customized half-body plaster casts have been used for patients requiring CSI and like treatments. These casts were relatively easy to make but required 2 days to dry before they became strong enough to support a patient's weight. In addition, to enter and exit the casts in the prone position, it was necessary for the patients to brace themselves with both arms on the cast. The pressure exerted on the cast was often more than the cast could tolerate. For many patients, particularly those with neurologic deficits, getting in and out of the cast was difficult. Another problem is the delay by 2 to 3 days in starting the treatments because the cast needed to dry before it was strong enough to support the patient's weight. Finally, the typical half-body plaster casts made it difficult for physicians to monitor a patients breathing or to connect breathing tubes because the cast would cover the patient's face. Attempts to clear passageways were difficult due to the nature of plaster and how it would react to attempted modification.

SUMMARY OF THE INVENTION

It is, therefore, a primary object of the present invention to provide an improved method and apparatus for immobilizing portions of the human anatomy and specifically the head, shoulder and torso region when the patient is in the prone position.

It is a further object of the present invention to provide an improved method and apparatus for creating an individualized mold for selected portions of the human body and especially the head, shoulder and torso region when the patient is in the prone position.

It is a further object of the present invention to provide an improved method and apparatus for immobilizing portions of the human anatomy which is comfortable when the patient is in the prone position.

It is a further object of the present invention to provide an improved method and apparatus for immobilizing portions of the human anatomy which provides an aperture for the patient's face when the patient is in the prone position.

It is a further object of the present invention to provide an improved method and apparatus for immobilizing portions of the human anatomy in the prone position which is easy for patients to enter and exit.

It is a further object of the present invention to provide an improved method and apparatus for immobilizing portions of the human anatomy in the prone position which can be formed and used substantially immediately for treatment that must begin immediately.

These and other objects and advantages are accomplished by an improved method and apparatus which in general comprises a base, a face support with an aperture, a pair of head side walls, a pair of shoulder walls, and a pair of body side walls. A foam mixture is applied to the upper surface of the base and attached components, and the entire device is placed into a large flexible container or bag. A patient's head, shoulder and torso region is placed on the device in a prone position. The patient remains in a fixed position while the foam mixture expands around the patient's head, body and the apparatus framework. After a brief period of time, the foam sets or hardens and a mold or template is formed.

In this manner, a mold or template is created which can be used to immobilize the head, shoulder and torso region of the human body in the prone position during certain medical procedures including X-rays, CAT-scans, MRI and other radiographic procedures and therapeutic treatment of patients using external radiation. The template is reused in similar subsequent procedures for placing that portion of the human body in the same position that it was in during the initial procedure, resulting in an increased ability for medical personnel to isolate, examine or treat a target area of the patient's body.

DETAILED DESCRIPTION OF THE PREFERRED EMBODIMENT

Figure 1:
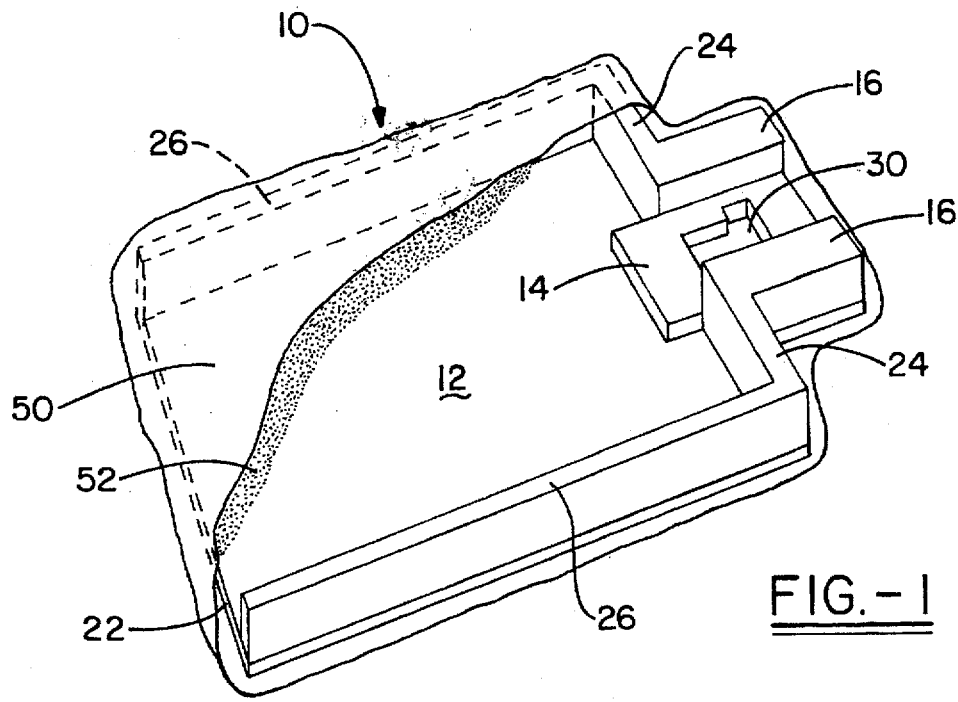
FIG. 1 is a perspective view of the apparatus for creating a template of the head, shoulder and torso region of the human anatomy when in the prone position according to the present invention.

Now with reference to the invention illustrated in the drawings and specifically FIG. 1, an apparatus for creating a mold or template for the head, shoulder and torso region of the human body in the prone position is shown generally by numeral 10. The template forming apparatus consists generally of an essentially planar base 12, a face support 14, a pair of head side walls 16, a pair of shoulder walls 24, a pair of body side walls 26, a flexible bag or container 50, and a foaming mixture 52.

Figure 2:
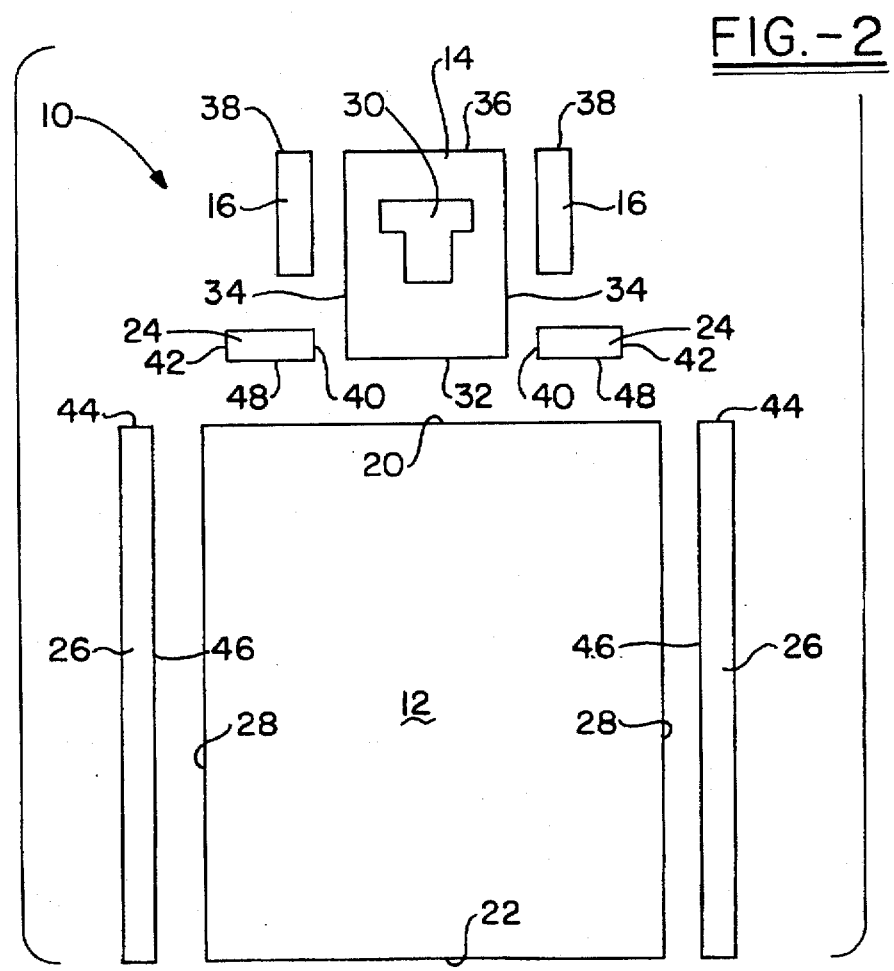
FIG. 2 is an assembly drawing illustrating the various components of the apparatus shown in FIG. 1.

Base 12, as shown in FIG. 2, is essentially rectangular in shape and has an upper surface 18, although it is appreciated that a variety of alternative shapes are possible. In the preferred embodiment planar base 12 is composed of an extruded polystyrene material sufficient to support the weight of a patient for which the mold is being created. Numerous other materials would be recognized as suitable by those of ordinary skill in the art.

In FIG. 2, a face support 14, preferably made from an expanded polystyrene material is attached to upper surface 18 of planar base 12 at or near its top 20 and centered. Only a small portion of face support 14 is attached to upper surface 18 of planar base 12. Although not required in the preferred embodiment, face support 14 is cantilevered from the top 20 of planar base 12. The gap between whatever surface planar base 12 is placed and face support 14 is enough to allow for breathing tubes to be connected to the patient during treatment. Face support 14 is attached to base 12 by means known in the art but preferably contact adhesive or double-sided tape products. In fact, all further parts of apparatus 10 are attached in the same or similar manner, contact adhesive or double-sided tape products, as base 12 and such attachment means will not be further discussed. Face support 14 may be fabricated from several pieces of polystyrene but in the preferred embodiment is fabricated from a single planar and rectangular block. On either side of face support 14 are head sidewalls 16 which are partially attached the upper surface 18 of planar base 12 and to the sides 34 of face support 14. When positioned properly, the tops 38 of head side walls 16 will be aligned linearly with the top 36 of face support 14. Head side walls 16 are attached and run parallel to sides 34 of face support 14. Shoulder walls 26 are attached to upper surface 18 of planar base 12 at its top 20 with inside ends 40 of shoulder walls 26 abutted against sides 34 of face support 14 and aligned perpendicular to head side walls 16. Body side walls 26 are attached to the upper surface 18 of planar base 12 along outer sides 28 of planar base 12. In the preferred embodiment, body side walls 26 are equal in length to planar base 12 so that when attached, tops 44 of body side walls 26 are aligned linearly with the top 20 of planar base 12. Also, once attached insides 46 of body side walls 26 are abutted to outside ends 42 of shoulder walls 24.

This arrangement of head side walls 16, shoulder walls 24 and body side walls 26 creates a retaining means used to keep foaming mixture 52, which will be discussed further, within apparatus 10. It is to be understood that the description of the preferred embodiment is not meant to limit the scope of the present invention. A person of ordinary skill in the art would understand that many different arrangements of head side walls 16, shoulder walls 24 and body side walls 26 could be used. For example all three of the different walls just mentioned could be in the form of a single continuous element or the lengths could be different such as having shoulder walls 24 extend to outer sides 28 of planar base 12 and then having top 44 of body side walls 26 abut the inside 48 of shoulder walls 24. The examples given are not to be interpreted as limiting the spirit or scope of the present invention.

Once face support 14, head side walls 16, shoulder walls 24, and body side walls 26 are positioned and attached to upper surface 18 of planar base 12, a foam mixture 52 is applied to apparatus 10.

Foam mixtures that are suitable for practice of the present invention are not in themselves particularly unique and may include the polyurethane family. Various formulations of the polyurethane family are employed to provide foams having widely disparate, ultimate characteristics. For example, some formulations provide foam that is hydrophilic and are, therefore, eminently suited to be used for supports for floral displays. Other formulations provide foam that possesses antipodal characteristics, and which are, therefore, eminently suited to be used in, or as, flotation devices.

In order to be suitable for use in medical applications, such as the present, foam compositions must exhibit a low foaming temperature so as not to create a potential of causing a burn to the patient. Further, it is desirable that any foam composition have a quick hardening time and have sufficient integrity to immobilize the particular body portion as well as support the necessary weight of the patient. One specific formulation which is well suited to this method and apparatus is the polyurethane foam composition set out in U.S. Pat. No. 4,771,082. This polyurethane foam composition has a maximum foaming temperature of 45 degrees Celsius and hardens in approximately 8–10 minutes.

The basic reaction is that of mixing a polyol and a polyisocyanate such as follows:

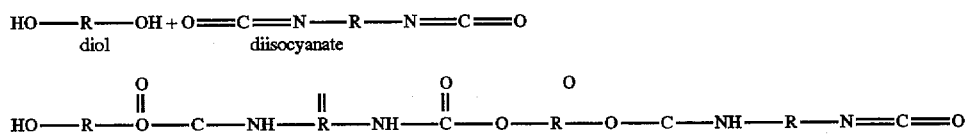

Surfactants, catalysts and blowing agents are generally added in various amounts selectively to provide the desired properties from the wide range available, including such characteristics as hydrophilia rate of rise, rate of cure, amount of heat release, cell size and rigidity. The preferred polyisocyanate for practice of the subject invention is polymethylenepolyvinyl isocyanate, whereas the preferred polyol is a mixture of various polyols such as ethylene glycol, glycerin 2,2 dimethyl-1,3-butanediol, 1,2,4 butanetriol, 1,2,6 hexanetriol and the like.

A typical application of the present invention to mold a template for any selected portion of a patient's anatomy would employ the addition of approximately 100 ml to 350 ml of the polyol to 75 ml to 240 ml of the polyisocyanate.

The chemicals required to form the foam are then mixed together. Typically the polyisocyanate is provided in a bottle larger than that required, and the bottle in which the polyol is provided is emptied into the bottle containing the polyisocyanate. The bottle now contains the mixed polyisocyanate and polyol is then capped and vigorously shaken for approximately 35 seconds. Thereafter, the bottle is opened and the contents are poured onto base 12. The foam mixture 52 is spread as evenly as possible over the base.

A barrier means is then placed over the entire upper surface 18 of the foam-containing apparatus 10. The barrier means is illustrated in FIG. 1 as a flexible container or bag 50 with the entire apparatus 10 contained therein. Ideally, air is allowed to circulate inside the bag until bubbles are noted in the foam (1–3 minutes). The air is then forced out, the bag is sealed and the patient is placed in the foam. However, a sheeted material placed over the entire upper surface 18 of apparatus 10 and insulating the patient from any contact with the foam mixture can be used. The barrier means must be tear-resistant, flexible and must not react with the selected foam mixture. A suitable barrier means may be fabricated from a pliable, sturdy material such as polyvinyl-chloride (PVC). Even though PVC has proven to be a perfectly acceptable material, it should be appreciated that the wall thickness of the bag should be no less than approximately 1.5 mils. Hence, some standard refuse bags, even though made of PVC, cannot be used because their wall thickness if too thin. Some industrial refuse bags, and certain brands of those home refuse bags advertised as having "double wall" thickness, or the like, as well as certain brands of waste compactor bags, however, do possess the requisite wall thickness, and they may be employed.

This minimal wall thickness is required to accomplish two objectives. First, a wall thickness of less than 1.5 mils is too subject to tearing or rupturing. Flexible container 50 must provide a controlled confinement for the foam mix, if the invention is to be satisfactorily employed, and the objective cannot be achieved if flexible container 50 ruptures, or tears. Second, a wall thickness of less than 1.5 mils is too susceptible to wrinkling and could cause an undesirable fold where it might not be visually detectable. Such unobserved folds can capture the foam mixture before it fully foams to create localized "hot spots" that could make the patient uncomfortable, at the least, or, at the worst, burn the patient. Such localized hot spots have been observed to melt the PVC bag at, and around, such a fold. Employing a PVC bag having sufficient wall thickness, however, has been found to obviate this potential problem.

A flattened bag measuring approximately 54×246 inches (137.2 by 61 cm) provides a convenient size that can be readily adapted to virtually any situation, as will become apparent from the hereinafter described exemplary usage.

It is to be understood that foam mixture 52 can be applied to apparatus 10, as previously explained, after apparatus 10 has been placed within a flexible container or bag 50.

Figure 4:
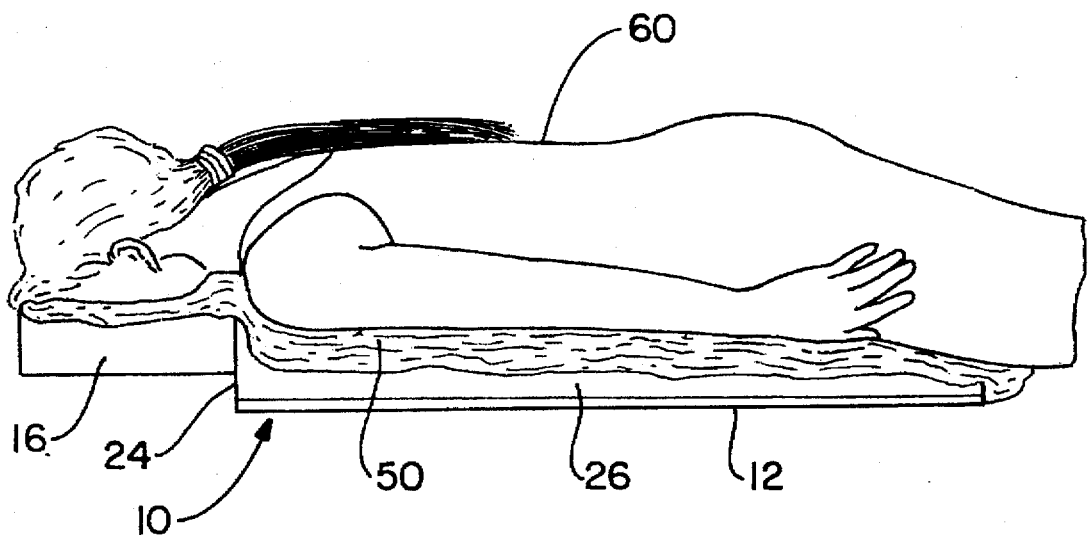
FIG. 4 is a perspective view of the apparatus shown in FIG. 1 showing a patient positioned in the apparatus in the prone position.

After foaming mixture 52 has been applied to upper surface 18 of base 12 and the barrier means applied, that portion of patient 60's body for which the template or mold is to be made is placed into contact with apparatus 10 as shown in FIG. 4. As foaming mixture 52 begins to expand and rise, it begins to pull a portion of barrier means 50 away from apparatus 10 and into conforming contact with patient 60's body portion. As the patient remains in a stable non-moving state, the foam hardens to form an impression of the particular body part. The foaming action typically subsides after about fifteen minutes, and thereafter, the patient can be carefully extricated from the newly formed mold. The mold should then be permitted to harden for a period of five to thirty minutes.

Figure 3:
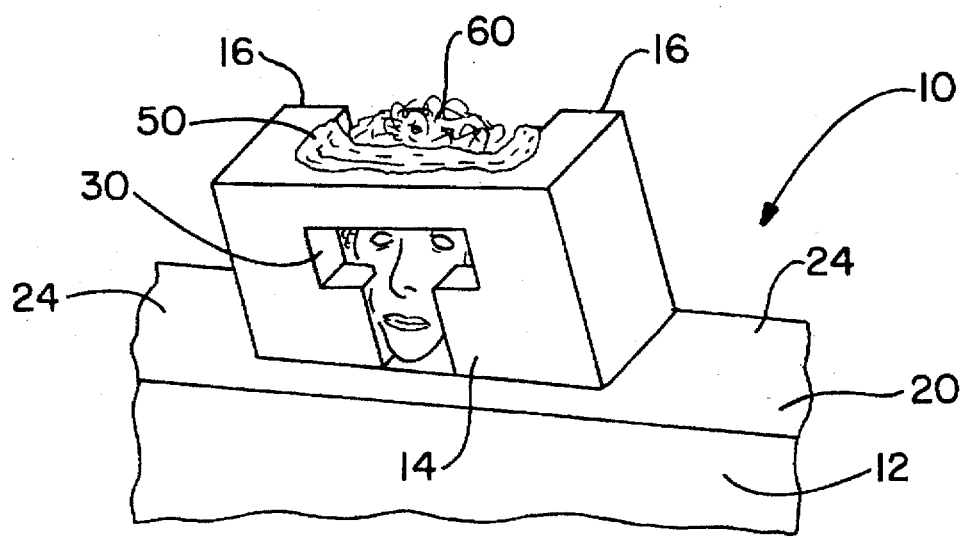
FIG. 3 is a perspective view of the apparatus shown in FIG. 1 viewed from the underside showing a patient in the prone position with the patient's face positioned in the aperture of the face support.

One important feature of apparatus 10 is aperture 30 in face support 14. Aperture 30 provides an unobstructed view of the patient's face and eyes while allowing sufficient airflow to the patient, both during the molding procedure and treatment. Aperture 30 can be made or modified into any shape necessary, as dictated by the individual patient's needs but in the preferred embodiment is an enlarged T-shape. The T-shaped opening allows the patient's eyes, nose and mouth to be constantly monitored throughout any radiation or examination procedure. Frequently, users place a mirror on the floor directly under the T-shaped opening in order to continually monitor the patient. Another advantage of the T-shaped opening is that it allows the frontal bone (forehead) and the zygomatic bone (cheek bones) to rest on the form thereby relieving pressure from the eyes, nose and mouth region. FIG. 3 shows face support 14 of apparatus 10 with patient 60 in the prone position. As shown, a clear and unobstructed aperture or passageway allows patient 60's eyes and nose to be accessed while positioned in apparatus 10. While not clearly shown in FIG. 3, flexible bag or container 50 is taped around aperture 30 of face support 14 and head side walls 16 forming a channel around patient 60's head. In fact, the present invention in effect molds around a significant portion of the patient's head. When flexible bag or container 50 is taped or secured around aperture 30 of face support 14 it is left loose above head side walls 16 on each side of the face portion to allow foaming mixture 52 to raise around the rear portion of the patient's skull. Foaming mixture 52 also raises up past the patient's hairline in the forehead region, generally up to the ears on each side of the patient's head. The resulting form not only allows the patient to be placed in a prone position but it immobilizes the skull and mandible which prevents inadvertent movement by the patient. Foaming mixture 52 will expand inside flexible bag or container 50 creating a face form which will maintain patient 60's head in a secure and easily reproducible position.

Once apparatus 10 is formed, upon reinsertion into the mold the particular portion of the patient's body to be examined will be returned or repositioned just as it was at the time of mold formation. The resulting apparatus or mold can be used in successive procedures involving the same portion of the body to consistently duplicate the previous positioning and immobilization. The template made in accordance with this invention can also be further modified for the type of treatment desired, for example, by cutting access holes directly through the template.

In the preferred embodiment of the present invention, planar base 12, face support 14, head side walls 16, shoulder walls 24 and body side walls 26 are made from extruded or expanded polystyrene materials because of the material's light weight, durability for this intended purpose and affordability. Even more importantly, polystyrene products are substantially radiolucent. In this way, transmission of irradiation treatment can take place through the apparatus and/or hardened foam with minimal, if any, interference or distortion. However, numerous other material could be used to accomplish the purposes of this invention. The elements of the present invention can be supplied in the form of a single kit for use with patients of varying size.

It should be apparent that the invention accomplishes the objects thereof. As stated, a variety of boards, supports, spacers, foam mixtures and methods of attaching to the base can be employed in the practice of this invention. It is to be understood that such variations are intended to fall within the scope of the claimed invention and that the subject invention is not to be limited by the specific method of operation described and/or depicted by the drawings nor is the invention to be limited by the specific chemical and mechanical components identified and described herein. There have been designated merely to provide a demonstration of operability and the selection of mechanically equivalent arrangements is not deemed a departure from the spirit of the invention being limited solely by the scope of the attached claims.

What is claimed is:

1. A method of forming a mold for prone positioning of the head, shoulder and torso region of the human anatomy comprising the steps of:
    a) providing a base structure including an apertured face support region, said apertured face support region being cantilevered from said base to provide access to a human's face whose head, shoulder and torso region are in a prone position;
    b) applying a foam mixture to the area of said base structure;
    c) placing a barrier means over said foam mixture;
    d) positioning said head, shoulder and torso region of the human anatomy onto said base structure with said face support region receiving the head in a prone position; and
    e) maintaining said head, shoulder and torso of the human anatomy in a fixed prone position for a sufficient length of time for said foam mixture to set and form a mold therefor.

2. The method of forming a mold as recited in claim 1 wherein said face support is a planar rectangular block.

3. The method of forming a mold as recited in claim 1 wherein said apertured face support is T-shaped and supports a patient's frontal bone and zygomatic bone when said patient's head is positioned in said face support in the prone position.

4. The method of forming a mold as recited in claim 1 wherein said barrier means comprise a flexible container for containing said foam mixture.

5. The method of forming a mold as recited in claim 4 comprising the further steps, inserted between steps (c) and (d), of:
    allowing air to circulate inside of said barrier means for a length of time; and expelling said air from said barrier means and sealing said barrier means.

6. The method of forming a mold as recited in claim 1 wherein said barrier means is attached to said apertured face support region in a loose manner thereby forming a channel which encircles said patient's face, said barrier means allowing said foaming mixture to raise up above and around said patient's head.

7. The method of forming a mold as recited in claim 6 wherein said barrier means is attached to said face support and around said aperture thereby leaving said aperture unencumbered by said barrier means.

8. The method of forming a mold as recited in claim 1, wherein said foam mixture is produced by mixing the contents of a first container means containing a polyol mixture to the contents of a second container means containing polyisocyanate.

9. The method of forming a mold as recited in claim 8, wherein the ratio of said polyol mixture to said polyisocyanate ranges from about 1:3 to about 5:1 by volume.

10. The method of forming a mold as recited in claim 1 wherein said base structure further comprises:
    a pair of head side walls, each of said head side walls is attached to either side of said face support.

11. The method of forming a mold as recited in claim 1 wherein said base structure, having an interior region and a periphery, further comprises a wall attached to said base and extending perpendicular along a portion of the periphery of said base structure.

12. A method of forming a mold for prone positioning of the head, shoulder and torso region of the human anatomy comprising the steps of:
    a) providing a base structure including an apertured face support region to receive the prone positioned head, said apertured face support region being cantilevered from said base to provide access to a human's face whose head, shoulder and torso region are in a prone position;
    b) placing a barrier means over said base structure;
    c) applying a foam mixture to the area between said barrier means and said base structure;
    d) positioning said head, shoulder and torso region of the human anatomy onto said base structure with said face support region receiving the head in a prone position; and
    e) maintaining said head, shoulder and torso of the human anatomy in a fixed prone position for a sufficient length of time for said foam mixture to set and form a mold therefor.

* * * * *